US009150934B2

(12) United States Patent
Hooper

(10) Patent No.: US 9,150,934 B2
(45) Date of Patent: Oct. 6, 2015

(54) **METHODS AND COMPOSITIONS FOR DETECTING *ASPERGILLUS TERREUS*, *ASPERGILLUS NIGER*, AND MYCOTOXINS**

(71) Applicant: Medical Service Consultation International LLC, Carollton, TX (US)

(72) Inventor: Dennis G. Hooper, Lewisville, TX (US)

(73) Assignee: Medical Service Consultation International, LLC, Carrollton, TX (US)

(*) Notice: Subject to any disclaimer, the term of this patent is extended or adjusted under 35 U.S.C. 154(b) by 0 days.

(21) Appl. No.: 14/590,151

(22) Filed: Jan. 6, 2015

(65) Prior Publication Data

US 2015/0125860 A1    May 7, 2015

Related U.S. Application Data

(63) Continuation of application No. 13/826,074, filed on Mar. 14, 2013, now Pat. No. 8,956,821.

(60) Provisional application No. 61/761,619, filed on Feb. 6, 2013.

(51) Int. Cl.
*C12Q 1/68* (2006.01)
*C12P 19/34* (2006.01)

(52) U.S. Cl.
CPC ........ *C12Q 1/6895* (2013.01); *C12Q 2600/112* (2013.01)

(58) Field of Classification Search
None
See application file for complete search history.

(56) References Cited

U.S. PATENT DOCUMENTS

| 4,683,202 | A  | 7/1987  | Mullis          |
| 4,744,981 | A  | 5/1988  | Pavansasivam    |
| 4,772,551 | A  | 9/1988  | Hart et al.     |
| 4,800,159 | A  | 1/1989  | Mullis et al.   |
| 4,906,452 | A  | 3/1990  | Sivam           |
| 5,261,394 | A  | 11/1993 | Mulligan et al. |
| 5,426,027 | A  | 6/1995  | Lott et al.     |
| 5,776,694 | A  | 7/1998  | Sheiness et al. |
| 6,210,345 | B1 | 4/2001  | Van Brunt       |
| 6,268,222 | B1 | 7/2001  | Chandler et al. |
| 6,345,025 | B1 | 2/2002  | Yamamiya        |
| 6,362,008 | B1 | 3/2002  | Kohn et al.     |
| 6,372,430 | B1 | 4/2002  | Morrison et al. |
| 6,696,304 | B1 | 2/2004  | Davies          |
| 6,699,670 | B2 | 3/2004  | Rothman et al.  |
| 6,846,631 | B2 | 1/2005  | Beck et al.     |
| 6,872,523 | B1 | 3/2005  | Iwen et al.     |
| 7,384,622 | B2 | 6/2008  | Hata et al.     |
| 8,628,928 | B2 | 1/2014  | Hooper          |
| 8,956,821 | B2 | 2/2015  | Hooper          |
| 8,962,251 | B2 | 2/2015  | Hooper          |
| 2001/0004813 | A1 | 6/2001 | Hedman        |
| 2003/0054356 | A1 | 3/2003 | Jacobson et al. |
| 2003/0129600 | A1 | 7/2003  | Morrison et al. |
| 2003/0203412 | A1 | 10/2003 | Vojdani         |
| 2004/0023207 | A1 | 2/2004  | Polansky        |
| 2004/0170981 | A1 | 9/2004  | McKenney et al. |
| 2005/0176023 | A1 | 8/2005  | Ramon et al.    |
| 2008/0014582 | A1 | 1/2008  | Hooper          |
| 2008/0108905 | A1 | 5/2008  | Lurie           |
| 2010/0068718 | A1 | 3/2010  | Hooper          |
| 2010/0075322 | A1 | 3/2010  | Hooper          |
| 2010/0129821 | A1 | 5/2010  | Fredricks       |
| 2011/0104684 | A1 | 5/2011  | Hooper          |
| 2013/0059307 | A1 | 3/2013  | Hooper          |
| 2013/0183697 | A1 | 7/2013  | Hooper          |
| 2014/0221504 | A1 | 8/2014  | Hooper          |
| 2014/0342927 | A1 | 11/2014 | Hooper          |

FOREIGN PATENT DOCUMENTS

| EP | 1215282         | 6/2002  |
| WO | WO96/21741      | 7/1996  |
| WO | WO98/50584      | 11/1998 |
| WO | WO01/54653      | 8/2001  |
| WO | WO2004/054359   | 7/2004  |
| WO | WO2007/023461   | 3/2007  |
| WO | WO 2008/051285  | 5/2008  |

OTHER PUBLICATIONS

Koster et al, "A geographically diverse set of isolates indicates two phylogenetic lineages within *Strachybotrys chartarum*," Can. J. Bot., 2003; 81: 633-643.
Niesters et al, "Rapid, polymerase chain reaction-based identification assays for *Candida* species," Journal of Clinical Microbiology, 1993, 904-910.
Chen et al, "Identification of medically important yeasts using PCR-based detection of DNA sequence polymorphisms in the internal transcribed spacer 2 region of the rRNA genes," Journal of Clinical Microbiology, 2000; 2302-2310.
Henry et al., "Identification of *Apsergillus* species using internal transcribed spacer regions 1 and 2," Journal of Clinical Microbiology, 2000; 1510-1515.
Fontelo, "Detection of T-2 toxin by an improved radioimmunoassay," Applied and Environmental Microbiology, 1983; 45(2):640-643.
Brasel et al, "Detection of airborne *Stachybotrys chartarum* macrocyclic trichothecene mycotoxins on particulates smaller than conidia," Applied and Environmental Microbiology, 2005; 71:114-122.
Kierek-Jaszcuk et al., "Detection and quantification of the T-2 mycotoxin by ELISA utilizing toxin-specific polyclonal antibodies raised in chickens," Food and Agricultural Immunology, 1995; 7:243-252.
Groopman et al, "High-affinity monoclonal antibodies for aflatoxins and their application to solid-phase immunoassays," P.N.A.S., 1984; 81:7728-7731.
Vetro, Thesis: Development of sensitive immunodiagnostics for determination of toxic residues (mycotoxins, drugs) in biological fluids and animal feeds, 2002.
Lewis et al., "Detection of gliotoxin in experimental and human aspergillosis," *Infection and Immunity*; 2005; 73(1): 635-637.

(Continued)

*Primary Examiner* — Jehanne Sitton
(74) *Attorney, Agent, or Firm* — Barnes & Thornburg LLP

(57) ABSTRACT

The invention relates to a method of identifying an *Aspergillus terreus* or an *Aspergillus niger* fungal species in patient tissue or body fluid and to primers and probes for use in such a method.

10 Claims, No Drawings

(56) References Cited

OTHER PUBLICATIONS

Spiess et al., "Development of a LightCycler PCR assay for detection and qualification of *Aspergillus fumigatus* DNA in clinical samples from neutropenic patients," *Journal of Clinical Microbiology*, 2003; 41(5): 1811-1818.
Fox et al., "Detection of *Aspergillus fumigatus* mycotoxins: immunogen synthesis and immunoassay development," *Journal of Microbiological Methods*, 2004; 6+: 221-230.
Bialek et al., "PCR based identification and discrimination of agents of mucomycosis and aspergillosis in paraffin wax embedded tissue," *J. Clin. Pathol.*, 2005; 58:1180-1184.
Zorgani et al.,., "Detection pyrogenic toxin of *Staphylococcus aureus* in sudden infant death syndrome," *FEMS Immunology and Medical Microbiology*, 1999; 25: 103-108.
Stack et al., "Nonribosomal peptide synthesis in *Apergillus fumigates* and other fungi," *Microbiology*, 2007; 153(5): 1297-1306.
Ferns, "Evaluation of the role of real-time PCR in the diagnosis of invasive aspergillosis," *Leukemia & Lymphoma*, 2006; 41(1): 15-20.
Cruz-Perez et al., Detection and quantitation of *Aspergillus fumigatus* in pure culture using polymerase chain reaction, *Molecular and Cellular Probes*, 2001; 15:81-88.
GenBank AF138288 [online] Apr. 11, 2000 [retrieved on Feb. 23, 2012] retrieved from http://www.ncbi.nlm.nih.gov/nuccore/af138288.
De Vries et al. "*Aspergillus vadensis*, a new species of the group of black Aspergilli," Antoine Van Leeuwenhoek, 2005; 87(3): 195-203.
Ahern, *The Scientist*, 1995; 20(15):1-9.
Nielsen et al., "Yeast populations associated with Ghanaian cocoa fermentations analyzed using denaturing gradient gel electrophoresis (DGGE)," *Yeast*; 2005; 22:271-284.
Bennett et al., "Mycotoxins," *Clin. Microbiol. Rev.*, 2003; 16(3):497-516.
Lee et al., J. Assoc. Off. Anal. Chem., 1989, 72(2): 345-348.
Brasel at el., Archives of Environmental Health: An international Journal, Jun. 2004, 59(6): 317-323.
Zinkevich et al., FEMS Microbiology Ecology, 2000, 34: 147-155.
Andersson et al., Appl Environ Microbiol, 1997, 63(2): 387-393.
Quatrini et al., Hydrometallurgy, 2006, 83: 263-272.
Wulf-Durand et al., Appl. Environ. Microbiol., 1997, 63(7): 2944-2948.
Gregory et al., Toxicology Pathol., 2004, 32: 26-34.
Lee et al., J. Agric. Food Chem., 1990, 38: 444-448.
QuantiTox Kit from EviroLogix (Jul. 12, 2004).
Llobet-Brossa et al., Aquatic Microbial Ecol, 2002, 29: 211-226.
Yamanaka, Biochemistry and Environmental Biology: Chemolitho-autotrophic Bacteria, 2008, pp. 7-9.
Bata et al., Appl Environ Microbiol, Mar. 1985, 49(3): 678-681.
McCormick et al., Toxins, 2011, 3: 802-814.
Willinger et al., Journal of Clinical Microbiology, 2003, 41(2): 581-585.
U.S. Appl. No. 14/590,173, unpublished.
De Aguirre et al., Journal of Clinical Microbiology, 2004, 42(8): 3495-3504.
Hinrikson et al., Journal of Clinical Microbiology, 2005, 43(5): 2092-2103.
GenBank AF 138287 [online] Apr. 11, 2000 [retrieved Sep. 20, 2014] retrieved from http://www.ncbi.nlm.nih.gov/nuccore/af138287.
Wei et al., Anal Biochem., Feb. 1987, 160(2): 399-408.
Brasilerio et al., "Genetic variability within *Fusarium solani* specie as revealed by PCR-fingerprinting based on pcr markers," Brazilian Journal of Microbiology, 2004, 35: 205-210.
Suga et al., "Phylogenetic analysis of the phytopathogenic fungus *Fusarium solani* cased on the rDNA-ITS region," Mycological Research, 2000, 104(10): 1175-1183.
Haugland et al., "Identification of putative sequence specific PCR primers for detection of the toxigenic fungal species *Stachybotrys chartarum*," Mol Cell Probes, Dec. 1998, 12(6): 387-96.
Mackay et al., "Real-time PCR in the microbiology laboratory," Clin. Microbiol. Infect., 2004, 10: 190-212.
International Search Report/Written Opinion for PCT/US07/08249, dated Oct. 17, 2008.

METHODS AND COMPOSITIONS FOR DETECTING *ASPERGILLUS TERREUS*, *ASPERGILLUS NIGER*, AND MYCOTOXINS

CROSS REFERENCE TO RELATED APPLICATIONS

This application is a continuation of U.S. application Ser. No. 13/826,074, filed Mar. 14, 2013, which claims priority under 35 U.S.C §119(e) to U.S. Provisional Application Ser. No. 61/761,619, filed on Feb. 6, 2013, the disclosures of which are herein incorporated by reference.

SEQUENCE LISTING

The instant application contains a Sequence Listing which has been submitted in ASCII format via EFS-Web and is hereby incorporated by reference in its entirety. Said ASCII copy, created on May 30, 2013, is named 41646-224546_SL.txt and is 4,378 bytes in size.

FIELD OF THE INVENTION

This invention relates to methods and compositions for detecting or identifying *Aspergillus terreus* DNA, *Aspergillus terreus* mycotoxins, *Aspergillus niger* DNA, and *Aspergillus niger* mycotoxins. More particularly, the invention relates to methods and compositions for detecting or identifying *Aspergillus terreus* DNA, *Aspergillus terreus* mycotoxins, *Aspergillus niger* DNA, and *Aspergillus niger* mycotoxins in the tissues or body fluid samples of patients.

BACKGROUND AND SUMMARY

Molds (i.e., toxigenic and other septate molds) are ubiquitous in the environment. Mold is the common name for various types of fungi. Molds are usually found in moist, warm environments. Because molds grow in wet or moist indoor environments, people are exposed to molds or their byproducts through either direct contact, or through the air, if molds or mold byproducts are aerosolized. Exposure to molds can cause a number of adverse effects including allergic reactions, asthma attacks, and infections, particularly in individuals with immune system deficiencies.

Adverse effects from molds may occur when individuals are exposed to large doses of chemicals, known as mycotoxins, which are fungal metabolites (Samson et al., 1985; Burge, 1990; Flannigan et al., 1991). Mycotoxins have toxic effects ranging from severe irritations, such as allergic reactions and asthma, to immuno-suppression and cancer. Most mycotoxins are cytotoxic and exert their effects by interfering with vital cellular processes such as protein, RNA, and DNA synthesis. As a result, mycotoxins may be damaging to the skin, the lungs, the gut, and the like. The combined outcome may increase the susceptibility of the exposed individual to infectious diseases and, possibly, to cancer. Almost all of the studies to date focus on disease induced by mycotoxins ingested in contaminated food (Baxter et al., 1981), but mycotoxins are secondary metabolites of fungal spores and can enter the body through the respiratory tract.

In heavily contaminated environments, neurotoxic symptoms related to airborne mycotoxin exposure have been reported (Croft et al., 1986). Skin is another potential route of exposure to the mycotoxins of several fungi which have caused cases of severe dermatosis (Vennewald and Wollina, 2005). These same molds may cause invasive mold infection among patients with diseases which render the patient immuno-suppressed such as leukemia, lymphoma, and many cancers (Kontoyiannis, D P et al, 2005). The mold infections in such patients are often fatal with a documented fatally rate of 92% (Paterson and Singh, 1999).

*Aspergillus terreus* is a species of fungus that is widespread throughout the world and may be found in warm arable soils. *Aspergillus terreus* is known to cause opportunistic infections in patients, particularly patients with deficient immune systems. For example, patients who have received a transplant are susceptible to infection caused by *Aspergillus terreus*. Importantly, infection with *Aspergillus terreus* is more likely to result in invasive, disseminated disease than infection with other *Aspergillus* species.

A definitive and early diagnosis of a fungal infection, such as a fungal infection caused by *Aspergillus terreus*, is crucial for patient treatment and management. A diagnosis of a fungal infection is often rendered late in the disease process, often even as late as autopsy (Kontoyiannis et al, 2000; Vogeser et al., 1997). The reasons for the late diagnosis of fungal infections include the lack of good clinical specimens, the difficultly in differentiating invasive mold infections from other types of infections, the lack of identification of molds with special stains in pathological specimens (i.e., these assays have a high error rate, a low sensitivity, and low specificity), and the lack of an ability to obtain an antibody-based diagnosis in immuno-compromised patients.

*Aspergillus niger* is a common species of fungus that is ubiquitous in soil and is also commonly found in indoor environments. *Aspergillus niger* is a common contaminant of various foods, for example fruits such as grapes and vegetables such as onions, as well as peanuts. Furthermore, *Aspergillus niger* is known to cause infections in patients, for example aspergillosis (a serious lung disease) and otomycosis (a fungal ear infection), as well as infections occurring in the endocardium, kidneys, respiratory tract, and digestive tract.

Thus, a reliable, sensitive, specific, and rapid method for *Aspergillus terreus* detection and *Aspergillus niger* detection in patient body fluids and tissues is needed. Applicant's present invention is based on the development of a reliable, sensitive, specific, and rapid method for detecting *Aspergillus terreus* DNA and *Aspergillus niger* DNA in patient body fluids and tissues. Furthermore, the method for detecting *Aspergillus terreus* DNA in patient body fluids and tissues can be combined with detection of an *Aspergillus terreus* mycotoxin. If *Aspergillus terreus* DNA or mycotoxins can be identified in patient tissue or body fluids, the identification may serve as a potential diagnostic method 1) to identify patients at risk for developing disease states related to *Aspergillus terreus* infections, or 2) to rapidly determine the cause of diseases related to *Aspergillus terreus* infections so that effective treatment regimens can be developed for patients exposed to molds and experiencing symptoms resulting from mold infection. The same applies to detection of *Aspergillus niger* DNA and mycotoxins.

The present invention provides methods for detecting and identifying, in patient tissue and patient body fluid specimens, 1) *Aspergillus terreus* DNA from fungal spores, 2) mycotoxins produced by *Aspergillus terreus*, 3) *Aspergillus niger* DNA from fungal spores, and 4) mycotoxins produced by *Aspergillus niger*. The present invention provides reliable, sensitive, and specific diagnostic tests for the presence of *Aspergillus, Aspergillus niger, Aspergillus terreus* fungal toxins, and *Aspergillus niger* fungal toxins in patient tissue and body fluids. The Applicant has developed *Aspergillus terreus* mycotoxin, *Aspergillus terreus* DNA, *Aspergillus niger* mycotoxin, and *Aspergillus niger* DNA extraction procedures and has supplemented those methods by developing detection methods. The detection methods employ antibody-based identification for mycotoxins and, for *Aspergillus terreus* DNA or *Aspergillus niger* DNA, the use of amplification of DNA with primers that specifically and selectively amplify *Aspergillus terreus* DNA or *Aspergillus niger* DNA isolated from patient tissues and body fluids.

The following embodiments are contemplated and are non-limiting:

1. A method of identifying an *Aspergillus terreus* fungal species in a patient tissue or a patient body fluid, the method comprising the steps of:
   extracting and recovering DNA of the *Aspergillus terreus* fungal species from the patient tissue or the patient body fluid;
   amplifying the DNA;
   hybridizing a probe to the DNA to specifically identify the fungal species, wherein the probe has a sequence consisting of SEQ ID NO: 1; and
   specifically identifying the *Aspergillus terreus* fungal species.

2. The method of clause 1, wherein the amplifying step is performed with primers that hybridize to the DNA.

3. The method of clause 1 or clause 2, further comprising using a forward primer and a reverse primer to amplify the DNA, wherein the forward primer consists of a sequence of SEQ ID NO: 2 and the reverse primer consists of a sequence of SEQ ID NO: 3.

4. The method of any one of clauses 1 to 3, wherein the DNA is amplified using PCR.

5. The method of clause 4, wherein the PCR is real-time PCR.

6. The method of any one of clauses 1 to 5, wherein the probe is fluorescently labeled.

7. The method of any one of clauses 1 to 6, wherein the probe is bound to a bead dyed with a fluorochrome.

8. The method of any one of clauses 1 to 7, wherein the amplified DNA is internal transcribed spacer regions of nuclear ribosomal DNA.

9. The method of any one of clauses 1 to 8, wherein the body fluid is selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma.

10. The method of any one of clauses 1 to 9, wherein the method further comprises the step of administering an anti-fungal agent to the patient.

11. The method of any one of clauses 1 to 10, wherein the method further comprises the step of testing for the presence of an *Aspergillus terreus* mycotoxin in the patient tissue or the patient body fluid prior to extraction and recovery of the DNA.

12. The method of any one of clauses 1 to 11, wherein the patient is a transplant patient.

13. A method of identifying a patient at risk for an *Aspergillus terreus* fungal infection, the method comprising the steps of:
   extracting and recovering DNA of the *Aspergillus terreus* fungal species from a tissue or a body fluid of the patient;
   amplifying the DNA;
   hybridizing a probe to the DNA to specifically identify the *Aspergillus terreus* fungal species, wherein the probe consists of a sequence of SEQ ID NO: 1; and
   specifically identifying the *Aspergillus terreus* fungal species.

14. The method of clause 13, wherein the body fluid is selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma.

15. The method of clause 13 or clause 14, wherein the probe is bound to a bead dyed with a fluorochrome.

16. The method of any one of clauses 13 to 15, wherein the method further comprises the step of developing an effective treatment regimen for the patient.

17. The method of any one of clauses 13 to 16, wherein the method further comprises the step of administering an anti-fungal agent to the patient.

18. The method of any one of clauses 13 to 17, wherein the method further comprises the step of testing for the presence of an *Aspergillus terreus* mycotoxin in the tissue or the body fluid prior to extraction and recovery of the DNA.

19. The method of clause 18, wherein the testing for the presence of the *Aspergillus terreus* mycotoxin comprises contacting the mycotoxin with an antibody directed against the mycotoxin.

20. The method of any one of clauses 13 to 19, wherein the patient is a transplant patient.

21. A method of identifying a patient with an *Aspergillus terreus* fungal infection, the method comprising the steps of:
   extracting and recovering DNA of the *Aspergillus terreus* fungal species from a tissue or a body fluid of the patient;
   amplifying the DNA;
   hybridizing a probe to the DNA to specifically identify the *Aspergillus terreus* fungal species, wherein the probe consists of a sequence of SEQ ID NO: 1; and
   specifically identifying the *Aspergillus terreus* fungal species.

22. The method of clause 21, wherein the body fluid is selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma.

23. The method of clause 21 or clause 22, wherein the probe is bound to a bead dyed with a fluorochrome.

24. The method of any one of clauses 21 to 23, wherein the method further comprises the step of developing an effective treatment regimen for the patient.

25. The method of any one of clauses 21 to 24, wherein the method further comprises the step of administering an anti-fungal agent to the patient.

26. The method of any one of clauses 21 to 25, wherein the method further comprises the step of testing for the presence of an *Aspergillus terreus* mycotoxin in the tissue or the body fluid prior to extraction and recovery of the DNA.

27. The method of clause 26, wherein the testing for the presence of the *Aspergillus terreus* mycotoxin comprises contacting the mycotoxin with an antibody directed against the mycotoxin.

28. The method of any one of clauses 21 to 27, wherein the patient is a transplant patient.

29. An isolated purified nucleic acid comprising SEQ ID NO: 1 or a sequence that hybridizes under highly stringent conditions to a sequence comprising SEQ ID NO: 1.

30. An isolated, purified nucleic acid consisting of SEQ ID NO: 1 or a sequence that hybridizes under highly stringent conditions to a sequence consisting of SEQ ID NO: 1.

31. An isolated, purified nucleic acid comprising SEQ ID NO: 2 or a sequence that hybridizes under highly stringent conditions to a sequence comprising SEQ ID NO: 2.

32. An isolated, purified nucleic acid consisting of SEQ ID NO: 2 or a sequence that hybridizes under highly stringent conditions to a sequence consisting of SEQ ID NO: 2.

33. An isolated, purified nucleic acid comprising SEQ ID NO: 3 or a sequence that hybridizes under highly stringent conditions to a sequence comprising SEQ ID NO: 3.

34. An isolated, purified nucleic acid consisting of SEQ ID NO: 3 or a sequence that hybridizes under highly stringent conditions to a sequence consisting of SEQ ID NO: 3.

35. A kit comprising an isolated, purified nucleic acid with a sequence comprising SEQ ID NO: 1.

36. A kit comprising an isolated, purified nucleic acid with a sequence consisting of SEQ ID NO: 1.

37. The kit of clause 35 or clause 36 further comprising a purified nucleic acid with a sequence comprising SEQ ID NO: 2 and a purified nucleic acid with a sequence comprising SEQ ID NO: 3.

38. The kit of clause 35 or clause 36 further comprising an isolated, purified nucleic acid with a sequence consisting of SEQ ID NO: 2 and an isolated, purified nucleic acid with a sequence consisting of SEQ ID NO: 3.

39. The kit of any one of clauses 35 to 38 further comprising components for the extraction and recovery of an *Aspergillus terreus* mycotoxin from a body fluid or a tissue of a patient and components for identification of the mycotoxin.

40. The kit of clause 39 wherein the components for identification of the mycotoxin include beads dyed with a fluorochrome and coupled to antibodies to the mycotoxin or to the mycotoxin or to a mycotoxin antigen.

41. The kit of clause 39 wherein the components for identification of the mycotoxin comprise an antibody directed against the mycotoxin.

42. A method of identifying an *Aspergillus niger* fungal species in a patient tissue or a patient body fluid, the method comprising the steps of:
extracting and recovering DNA of the *Aspergillus niger* fungal species from the patient tissue or the patient body fluid;
amplifying the DNA;
hybridizing a probe to the DNA to specifically identify the fungal species, wherein the probe has a sequence consisting of SEQ ID NO: 4; and
specifically identifying the *Aspergillus niger* fungal species.

43. The method of clause 42, wherein the amplifying step is performed with primers that hybridize to the DNA.

44. The method of clause 42 or clause 43, further comprising using a forward primer and a reverse primer to amplify the DNA, wherein the forward primer consists of a sequence of SEQ ID NO: 5 and the reverse primer consists of a sequence of SEQ ID NO: 6.

45. The method of any one of clauses 42 to 44, wherein the DNA is amplified using PCR.

46. The method of clause 45, wherein the PCR is real-time PCR.

47. The method of any one of clauses 42 to 46, wherein the probe is fluorescently labeled.

48. The method of any one of clauses 42 to 47, wherein the probe is bound to a bead dyed with a fluorochrome.

49. The method of any one of clauses 42 to 48, wherein the amplified DNA is internal transcribed spacer regions of nuclear ribosomal DNA.

50. The method of any one of clauses 42 to 49, wherein the body fluid is selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma.

51. The method of any one of clauses 42 to 50, wherein the method further comprises the step of administering an antifungal agent to the patient.

52. The method of any one of clauses 42 to 51, wherein the method further comprises the step of testing for the presence of an *Aspergillus niger* mycotoxin in the patient tissue or the patient body fluid prior to extraction and recovery of the DNA.

53. The method of any one of clauses 42 to 52, wherein the patient is a transplant patient.

54. A method of identifying a patient at risk for an *Aspergillus niger* fungal infection, the method comprising the steps of:
extracting and recovering DNA of the *Aspergillus niger* fungal species from a tissue or a body fluid of the patient;
amplifying the DNA;
hybridizing a probe to the DNA to specifically identify the *Aspergillus niger* fungal species, wherein the probe consists of a sequence of SEQ ID NO: 4; and
specifically identifying the *Aspergillus niger* fungal species.

55. The method of clause 54, wherein the body fluid is selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma.

56. The method of clause 54 or clause 55, wherein the probe is bound to a bead dyed with a fluorochrome.

57. The method of any one of clauses 54 to 56, wherein the method further comprises the step of developing an effective treatment regimen for the patient.

58. The method of any one of clauses 54 to 57, wherein the method further comprises the step of administering an antifungal agent to the patient.

59. The method of any one of clauses 54 to 58, wherein the method further comprises the step of testing for the presence of an *Aspergillus niger* mycotoxin in the tissue or the body fluid prior to extraction and recovery of the DNA.

60. The method of clause 59, wherein the testing for the presence of the *Aspergillus niger* mycotoxin comprises contacting the mycotoxin with an antibody directed against the mycotoxin.

61. The method of any one of clauses 54 to 60, wherein the patient is a transplant patient.

62. A method of identifying a patient with an *Aspergillus niger* fungal infection, the method comprising the steps of:
extracting and recovering DNA of the *Aspergillus niger* fungal species from a tissue or a body fluid of the patient;
amplifying the DNA;
hybridizing a probe to the DNA to specifically identify the *Aspergillus niger* fungal species, wherein the probe consists of a sequence of SEQ ID NO: 4; and
specifically identifying the *Aspergillus niger* fungal species.

63. The method of clause 62, wherein the body fluid is selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma.

64. The method of clause 62 or clause 63, wherein the probe is bound to a bead dyed with a fluorochrome.

65. The method of any one of clauses 62 to 64, wherein the method further comprises the step of developing an effective treatment regimen for the patient.

66. The method of any one of clauses 62 to 65, wherein the method further comprises the step of administering an antifungal agent to the patient.

67. The method of any one of clauses 62 to 66, wherein the method further comprises the step of testing for the presence of an *Aspergillus niger* mycotoxin in the tissue or the body fluid prior to extraction and recovery of the DNA.

68. The method of clause 67, wherein the testing for the presence of the *Aspergillus niger* mycotoxin comprises contacting the mycotoxin with an antibody directed against the mycotoxin.

69. The method of any one of clauses 62 to 68, wherein the patient is a transplant patient.

70. An isolated purified nucleic acid comprising SEQ ID NO: 4 or a sequence that hybridizes under highly stringent conditions to a sequence comprising SEQ ID NO: 4.

71. An isolated, purified nucleic acid consisting of SEQ ID NO: 4 or a sequence that hybridizes under highly stringent conditions to a sequence consisting of SEQ ID NO: 4.

72. A kit comprising an isolated, purified nucleic acid with a sequence comprising SEQ ID NO: 4.

73. A kit comprising an isolated, purified nucleic acid with a sequence consisting of SEQ ID NO: 4.

74. The kit of clause 72 or clause 73 further comprising a purified nucleic acid with a sequence comprising SEQ ID NO: 5 and a purified nucleic acid with a sequence comprising SEQ ID NO: 6.

75. The kit of clause 72 or clause 73 further comprising an isolated, purified nucleic acid with a sequence consisting of SEQ ID NO: 5 and an isolated, purified nucleic acid with a sequence consisting of SEQ ID NO: 6.

76. The kit of any one of clauses 72 to 75 further comprising components for the extraction and recovery of an *Aspergillus niger* mycotoxin from a body fluid or a tissue of a patient and components for identification of the mycotoxin.

77. The kit of clause 76 wherein the components for identification of the mycotoxin include beads dyed with a fluorochrome and coupled to antibodies to the mycotoxin or to the mycotoxin or to a mycotoxin antigen.

78. The kit of clause 76 wherein the components for identification of the mycotoxin comprise an antibody directed against the mycotoxin.

In any of the above-described method embodiments for *Aspergillus terreus*, the probe can consist of SEQ ID NO: 1. In any of the above-described method embodiments for *Aspergillus terreus*, the primers can consist of SEQ ID NO: 2 or SEQ ID NO: 3.

In any of the above-described method embodiments for *Aspergillus niger*, the probe can consist of SEQ ID NO: 4. In any of the above-described method embodiments for *Aspergillus niger*, the primers can consist of SEQ ID NO: 5 or SEQ ID NO: 6.

In one illustrative embodiment, a method is provided of identifying an *Aspergillus terreus* fungal species in a patient tissue or a patient body fluid. The method comprises the steps of extracting and recovering DNA of the *Aspergillus terreus* fungal species from the patient tissue or the patient body fluid, amplifying the DNA, hybridizing a probe to the DNA to specifically identify the fungal species, wherein the probe has a sequence consisting of SEQ ID NO: 1, and specifically identifying the *Aspergillus terreus* fungal species.

In another embodiment, a method is provided of identifying a patient at risk for an *Aspergillus terreus* fungal infection. The method comprises the steps of extracting and recovering DNA of the *Aspergillus terreus* fungal species from a tissue or a body fluid of the patient, amplifying the DNA, hybridizing a probe to the DNA to specifically identify the *Aspergillus terreus* fungal species, wherein the probe consists of a sequence of SEQ ID NO: 1, and specifically identifying the *Aspergillus terreus* fungal species.

In yet another embodiment, a method is provided of identifying a patient with an *Aspergillus terreus* fungal infection. The method comprises the steps of extracting and recovering DNA of the *Aspergillus terreus* fungal species from a tissue or a body fluid of the patient, amplifying the DNA, hybridizing a probe to the DNA to specifically identify the *Aspergillus terreus* fungal species, wherein the probe consists of a sequence of SEQ ID NO: 1, and specifically identifying the *Aspergillus terreus* fungal species.

In another illustrative embodiment, an isolated purified nucleic acid is provided. In one embodiment, the nucleic acid comprises SEQ ID NO: 1 or a sequence that hybridizes under highly stringent conditions to a sequence comprising SEQ ID NO: 1. In another embodiment, the nucleic acid consists of SEQ ID NO: 1 or a sequence that hybridizes under highly stringent conditions to a sequence consisting of SEQ ID NO: 1. In yet another embodiment, the nucleic acid comprises SEQ ID NO: 2 or a sequence that hybridizes under highly stringent conditions to a sequence comprising SEQ ID NO: 2. In another embodiment, the nucleic acid consists of SEQ ID NO: 2 or a sequence that hybridizes under highly stringent conditions to a sequence consisting of SEQ ID NO: 2. In yet another embodiment, the nucleic acid comprises SEQ ID NO: 3 or a sequence that hybridizes under highly stringent conditions to a sequence comprising SEQ ID NO: 3. In another embodiment, the nucleic acid consists of SEQ ID NO: 3 or a sequence that hybridizes under highly stringent conditions to a sequence consisting of SEQ ID NO: 3.

In another embodiment, a kit is provided. The kit can comprise an isolated, purified nucleic acid with a sequence comprising SEQ ID NO: 1, or an isolated, purified nucleic acid with a sequence consisting of SEQ ID NO: 1. The kit can also comprise components for the extraction and recovery of DNA or an *Aspergillus terreus* mycotoxin and components for DNA amplification and instructions for use of the kit.

In one illustrative embodiment, a method is provided of identifying an *Aspergillus niger* fungal species in a patient tissue or a patient body fluid. The method comprises the steps of extracting and recovering DNA of the *Aspergillus niger* fungal species from the patient tissue or the patient body fluid, amplifying the DNA, hybridizing a probe to the DNA to specifically identify the fungal species, wherein the probe has a sequence consisting of SEQ ID NO: 4, and specifically identifying the *Aspergillus niger* fungal species.

In another embodiment, a method is provided of identifying a patient at risk for an *Aspergillus niger* fungal infection. The method comprises the steps of extracting and recovering DNA of the *Aspergillus niger* fungal species from a tissue or a body fluid of the patient, amplifying the DNA, hybridizing a probe to the DNA to specifically identify the *Aspergillus niger* fungal species, wherein the probe consists of a sequence of SEQ ID NO: 4, and specifically identifying the *Aspergillus niger* fungal species.

In yet another embodiment, a method is provided of identifying a patient with an *Aspergillus niger* fungal infection. The method comprises the steps of extracting and recovering DNA of the *Aspergillus niger* fungal species from a tissue or a body fluid of the patient, amplifying the DNA, hybridizing a probe to the DNA to specifically identify the *Aspergillus* niger fungal species, wherein the probe consists of a sequence of SEQ ID NO: 4, and specifically identifying the *Aspergillus niger* fungal species.

In another illustrative embodiment, an isolated purified nucleic acid is provided. In one embodiment, the nucleic acid comprises SEQ ID NO: 4 or a sequence that hybridizes under highly stringent conditions to a sequence comprising SEQ ID NO: 4. In another embodiment, the nucleic acid consists of SEQ ID NO: 4 or a sequence that hybridizes under highly stringent conditions to a sequence consisting of SEQ ID NO: 4. In yet another embodiment, the nucleic acid comprises SEQ ID NO: 5 or a sequence that hybridizes under highly stringent conditions to a sequence comprising SEQ ID NO: 5. In another embodiment, the nucleic acid consists of SEQ ID NO: 5 or a sequence that hybridizes under highly stringent conditions to a sequence consisting of SEQ ID NO: 5. In yet another embodiment, the nucleic acid comprises SEQ ID NO: 6 or a sequence that hybridizes under highly stringent conditions to a sequence comprising SEQ ID NO: 6. In another embodiment, the nucleic acid consists of SEQ ID NO: 6 or a sequence that hybridizes under highly stringent conditions to a sequence consisting of SEQ ID NO: 6.

In another embodiment, a kit is provided. The kit can comprise an isolated, purified nucleic acid with a sequence comprising SEQ ID NO: 4, or an isolated, purified nucleic acid with a sequence consisting of SEQ ID NO: 4. The kit can also comprise components for the extraction and recovery of DNA or an *Aspergillus niger* mycotoxin and components for DNA amplification and instructions for use of the kit.

DESCRIPTION OF THE ILLUSTRATIVE EMBODIMENTS

The present invention relates to methods and compositions for identifying or detecting the presence of *Aspergillus terreus* or *Aspergillus niger* in patient tissue or body fluids. The identification and detection methods are based on 1) amplification of *Aspergillus terreus* or *Aspergillus niger* DNA using a PCR-based method and 2) detection and/or quantification of *Aspergillus terreus* or *Aspergillus niger* mycotoxins in patient body fluids or tissues. The methods and compositions (e.g., primers and probes) for amplification of *Aspergillus terreus* or *Aspergillus niger* DNA are highly specific and sensitive and avoid co-amplification of or do not co-amplify non-specific human or animal nucleic acids.

The methods and compositions for testing for mycotoxins to detect and quantify *Aspergillus terreus* or *Aspergillus niger* mycotoxins are also very specific and sensitive. These methods and compositions utilize antibody-based identification of mycotoxins. In illustrative embodiments, Enzyme Linked Immunosorbant Assay (ELISA), or affinity chromatography can be used to detect mycotoxins produced by *Aspergillus terreus* or *Aspergillus niger*, as well as antibody-based assays such as Luminex®-based assays.

In various illustrative embodiments, body fluids that can be tested for the presence of *Aspergillus terreus* or *Aspergillus niger* DNA or mycotoxins, include, but are not limited to, urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, such as seminal fluid, lymph fluid, and whole blood, serum, or plasma. These samples can be prepared for testing as described herein. In various embodiments, tissue samples can include tissue biopsies of hospital patients or out-patients and autopsy specimens. As used herein, the term "tissue" includes, but is not limited to, biopsies, autopsy specimens, cell extracts, tissue sections, aspirates, tissue swabs, and fine needle aspirates.

In accordance with the invention the word "patient" means a human or an animal, such as a domestic animal (e.g., a dog or a cat). Accordingly, the methods and compositions disclosed herein can be used for both human clinical medicine and veterinary applications. Thus, the patient afflicted with a disease state related to a fungal infection can be a human, or in the case of veterinary applications, can be a laboratory, agricultural, domestic or wild animal. The present invention can be applied to patients including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, chickens, and wild animals in captivity such as bears, pandas, lions, tigers, leopards, elephants, zebras, giraffes, gorillas, dolphins, and whales.

In one illustrative embodiment, a method is provided of identifying an *Aspergillus terreus* fungal species in a patient tissue or a patient body fluid. The method comprises the steps of extracting and recovering DNA of the *Aspergillus terreus* fungal species from the patient tissue or the patient body fluid, amplifying the DNA, hybridizing a probe to the DNA to specifically identify the fungal species, wherein the probe has a sequence consisting of SEQ ID NO: 1, and specifically identifying the *Aspergillus terreus* fungal species.

In some embodiments, the amplifying step is performed with primers that hybridize to the DNA. In some embodiments, the method further comprises using a forward primer and a reverse primer to amplify the DNA. In one embodiment, the forward primer comprises a sequence of SEQ ID NO: 2 and the reverse primer comprises a sequence of SEQ ID NO: 3. In another embodiment, the forward primer consists of a sequence of SEQ ID NO: 2 and the reverse primer consists of a sequence of SEQ ID NO: 3.

In one illustrative embodiment, a method is provided of identifying an *Aspergillus niger* fungal species in a patient tissue or a patient body fluid. The method comprises the steps of extracting and recovering DNA of the *Aspergillus niger* fungal species from the patient tissue or the patient body fluid, amplifying the DNA, hybridizing a probe to the DNA to specifically identify the fungal species, wherein the probe has a sequence consisting of SEQ ID NO: 4, and specifically identifying the *Aspergillus niger* fungal species.

In some embodiments, the amplifying step is performed with primers that hybridize to the DNA. In some embodiments, the method further comprises using a forward primer and a reverse primer to amplify the DNA. In one embodiment, the forward primer comprises a sequence of SEQ ID NO: 5 and the reverse primer comprises a sequence of SEQ ID NO: 6. In another embodiment, the forward primer consists of a sequence of SEQ ID NO: 5 and the reverse primer consists of a sequence of SEQ ID NO: 6.

In various embodiments, the DNA is amplified using PCR. In some embodiments, the PCR is real-time PCR. Real-time PCR-based methods can be used to amplify the *Aspergillus terreus* or *Aspergillus niger* DNA and to detect and identify *Aspergillus terreus* or *Aspergillus niger* DNA by hybridization of the probe to the *Aspergillus terreus* or *Aspergillus niger* DNA. PCR is described in U.S. Pat. Nos. 4,683,202 and 4,800,159, incorporated herein by reference, and methods for PCR are well-known in the art. Real-time PCR combines amplification and simultaneous probe hybridization to achieve sensitive and specific detection of infectious molds (i.e., fungi) in real-time thereby providing instant detection of molds. In this embodiment, the time to detect or identify the *Aspergillus terreus* or *Aspergillus niger* and to obtain a diagnosis is greatly reduced. Real-time PCR is conducted according to methods well-known in the art. Exemplary probes and primers and their target DNAs for *Aspergillus terreus* that can be used in accordance with the invention are shown below. "Primer F" refers to a forward primer and "Primer R" refers to a reverse primer which are well-known terms in the art.

```
Target: Aspergillus terreus
Probe:
                                        (SEQ ID NO: 1)
5'-AGTCTGAGTGTGATTCTTTGCAATC Primer F:
                                        (SEQ ID NO: 2)
5'-ACATGAACCCTGTTCTGAAAG Primer R:
                                        (SEQ ID NO: 3)
5'-CCAAGAGATCCATTGTTGAAAG
```

An exemplary probe and primers for *Aspergillus niger* are shown below. "Primer F" refers to a forward primer and "Primer R" refers to a reverse primer which are well-known terms in the art.

```
Target: Aspergillus niger
Probe:
                                        (SEQ ID NO: 4)
5'-TGTCTATTGTACCCTGTTGCTTC Primer F:
                                        (SEQ ID NO: 5)
5'-CGTAGGTGAACCTGCGGAAG Primer R:
                                        (SEQ ID NO: 6)
5'-ATCGATGCCGGAACCAAGAG
```

In various embodiments, sample preparation (i.e., preparation of the *Aspergillus terreus* or *Aspergillus niger* DNA) involves rupturing the cells (e.g., cells of the tissue or fungal spores in patient body fluid or tissue) and isolating the *Aspergillus terreus* or *Aspergillus niger* DNA from the lysate. Techniques for rupturing cells and for isolation of DNA are well-known in the art. For example, cells may be ruptured by using a detergent or a solvent, such as phenol-chloroform. DNA may be separated from the lysate by physical methods including, but not limited to, centrifugation, pressure techniques, or by using a substance with affinity for DNA, such as, for example, silica beads. After sufficient washing, the isolated DNA may be suspended in either water or a buffer. In other embodiments, commercial kits are available, such as Quiagen™, Nuclisensm™, and Wizard™ (Promega), and Promegam™. Methods for isolating DNA are described in Sambrook et al., "Molecular Cloning: A Laboratory Manual", 3rd Edition, Cold Spring Harbor Laboratory Press, (2001), incorporated herein by reference. In embodiments where *Aspergillus terreus* or *Aspergillus niger* DNA is not detected because the patient does not have a fungal infection, DNA in the lysate from the patient can be treated similarly.

In various embodiments described herein, the primers and probes used for amplification of the target DNA and for detection and identification of *Aspergillus terreus* or *Aspergillus niger* DNA are oligonucleotides from about ten to about one hundred, more typically from about ten to about thirty or about twenty to about twenty-five base pairs long, but any suitable sequence length can be used. In illustrative embodiments, the primers and probes may be double-stranded or single-stranded, but the primers and probes are typically single-stranded. The primers and probes described herein are capable of specific hybridization, under appropriate hybridization conditions (e.g., appropriate buffer, ionic strength, temperature, formamide, or $MgCl_2$ concentrations), to a region of the target DNA. The primers and probes described herein may be designed based on having a melting temperature within a certain range, and substantial complementarity to the target DNA. Methods for the design of primers and probes are described in Sambrook et al., "Molecular Cloning: A Laboratory Manual", 3rd Edition, Cold Spring Harbor Laboratory Press, (2001), incorporated herein by reference.

In some embodiments, the primers and probes described herein for use in PCR can be modified by substitution, deletion, truncation, and/or can be fused with other nucleic acid molecules wherein the resulting primers and probes hybridize specifically to the intended targets and are useful in the methods described herein for amplification of the target DNAs. In other illustrative aspects, derivatives can also be made such as phosphorothioate, phosphotriester, phosphoramidate, and methyiphosphonate derivatives, that specifically bind to single-stranded DNA or RNA (Goodchild, et al., *Proc. Natl. Acad. Sci.* 83:4143-4146 (1986)).

In one embodiment, the invention encompasses isolated or substantially purified nucleic acids as probes for *Aspergillus terreus* or *Aspergillus niger* or probes to amplify *Aspergillus terreus* or *Aspergillus niger* DNA. A "purified" nucleic acid molecule is substantially free of other cellular material, or culture medium when produced by recombinant techniques, or substantially free of chemical precursors or other chemicals when chemically synthesized. An "isolated" nucleic acid is free of sequences that naturally flank the nucleic acid in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived, or can contain no sequences that naturally flank the nucleic acid in the genomic DNA of the organism.

Also within the scope of the invention are nucleic acids complementary to the probes and primers described herein, and those that hybridize to the nucleic acids described herein or those that hybridize to their complements under highly stringent conditions. In accordance with the invention "highly stringent conditions" means hybridization at 65° C. in 5×SSPE and 50% formamide, and washing at 65° C. in 0.5×SSPE. Conditions for low stringency and moderately stringent hybridization are described in Sambrook et al., "Molecular Cloning: A Laboratory Manual", 3rd Edition, Cold Spring Harbor Laboratory Press, (2001), incorporated herein by reference. In some illustrative aspects, hybridization occurs along the full-length of the nucleic acid.

In some embodiments, also included are nucleic acid molecules having about 60%, about 70%, about 75%, about 80%, about 85%, about 90%, about 95%, at least 96%, at least 97%, at least 98%, or at least 99% homology to the probes and primers described herein. Determination of percent identity or similarity between sequences can be done, for example, by using the GAP program (Genetics Computer Group, software; now available via Accelrys on http://www.accelrys.com), and alignments can be done using, for example, the ClustalW algorithm (VNTI software, InforMax Inc.). A sequence database can be searched using the nucleic acid sequence of interest. Algorithms for database searching are typically based on the BLAST software (Altschul et al., 1990). In some embodiments, the percent identity can be determined along the full-length of the nucleic acid.

As used herein, the term "complementary" refers to the ability of purine and pyrimidine nucleotide sequences to associate through hydrogen bonding to form double-stranded nucleic acid molecules. Guanine and cytosine, adenine and thymine, and adenine and uracil are complementary and can associate through hydrogen bonding resulting in the formation of double-stranded nucleic acid molecules when two nucleic acid molecules have "complementary" sequences. The complementary sequences can be DNA or RNA sequences. The complementary DNA or RNA sequences are referred to as a "complement."

Techniques for synthesizing the probes and primers described herein are well-known in the art and include chemical syntheses and recombinant methods. Such techniques are described in Sambrook et al., "Molecular Cloning: A Laboratory Manual", 3rd Edition, Cold Spring Harbor Laboratory Press, (2001), incorporated herein by reference. Primers and probes can also be made commercially (e.g., CytoMol, Sunnyvale, Calif. or Integrated DNA Technologies, Skokie, Ill.). Techniques for purifying or isolating the probes and primers described herein are well-known in the art. Such techniques are described in Sambrook et al., "Molecular Cloning: A Laboratory Manual", 3rd Edition, Cold Spring Harbor Laboratory Press, (2001), incorporated herein by reference. The primers and probes described herein can be analyzed by techniques known in the art, such as restriction enzyme analysis or sequencing, to determine if the sequence of the primers and probes is correct.

In various embodiments of the methods and compositions described herein, the probes and primers can be labeled, such as with fluorescent compounds, radioactive isotopes, antigens, biotin-avidin, colorimetric compounds, or other labeling agents known to those of skill in the art, to allow detection and quantification of amplified DNA, such as by Real-Time PCR.

In some embodiments, the probe is fluorescently labeled. In illustrative embodiments, the labels may include 6-carboxyfluorescein (FAM™), TET™ (tetrachloro-6-carboxyfluorescein), JOE™ (2,7,-dimethoxy-4,5-dichloro-6-carboxyfluorescein), VIC™, HEX (hexachloro-6-carboxyfluorescein), TAMRA™ (6-carboxy-N,N,N',N'-tetramethylrhodamine), BHQ™, SYBR® Green, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein, Oregon Green 488, Oregon Green 500, Oregon Green 514, Pacific Blue, REG, Rhodamine Green, Rhodamine Red, ROX, and/or Texas Red. In some embodiments, the probe is bound to a bead dyed with a fluorochrome.

In some embodiments, the probes and primers described herein can be specific. In other embodiments, there are no cross-over reactions or cross-over detection for the probe and primer sequences described herein. Thus, the methods and compositions (e.g., primers and probes) for amplification of *Aspergillus terreus* or *Aspergillus niger* DNA can, in some embodiments, be highly specific. In other embodiments, co-amplification of non-specific nucleic acids can be avoided. In some embodiments, the amplified DNA is internal transcribed spacer regions of nuclear ribosomal DNA.

In various embodiments, the method further comprises the step of administering an anti-fungal agent to the patient. Exemplary patients include cancer patients, post-operative patients, transplant patients, patients undergoing chemotherapy, immunosuppressed patients, and the like. In one embodiment, the patient is a transplant patient. Patients may experience symptoms of fungal infections including sinusitis, allergic reactions, headaches, and skin rashes. Patients include humans or animals.

In another illustrative embodiment, the method further comprises the step of testing for the presence of an *Aspergillus terreus* or *Aspergillus niger* mycotoxin in the patient tissue or the patient body fluid prior to or after extraction and recovery of the DNA. In another embodiment, mycotoxin testing is done in the absence of DNA testing. In one embodiment, the method comprises the steps of extracting and recovering the mycotoxin from the patient tissue or body fluid, contacting the mycotoxin with an antibody directed against the mycotoxin, and identifying the myocotoxin. Methods of testing for mycotoxins in patient tissue or body fluid are described, for example, in U.S. patent application Ser. No. 11/731,674 (published as U.S. Patent Publication No. US 2008/0014582), herein incorporated by reference in its entirety.

*Aspergillus terreus* mycotoxins are known in the art, including, for example, citreviridin, citrinin, emodin, archin, emodol, frandulic acid, gliotoxinm patulin, phthiolic acid, terreic acid, terrain, terretonin, territrem A, and the like. Any mycotoxin associated with *Aspergillus terreus* can be identified in this embodiment.

*Aspergillus niger* mycotoxins are known in the art, including, for example, Malformin, Oxalic acid, Malformin, Ochratoxin A, 3-Furanacetic Acid, Asnipyrone A, Asnipyrone B, Butanedioic Acid, Deacetylaustin, Dehydroaustin, Ethanedioc Acid, Fumonisin B2, Fumonisin B4, Gliotoxin, Malformin, Nigerapyrone A, Nigerapyrone B, Orlandin, Phthioic Acid, and the like. Any mycotoxin associated with *Aspergillus niger* can be identified in this embodiment.

Illustratively, patient (e.g., human or animal) tissue is received in 1) a 10% formalin fluid or 2) in a paraffin block in which the tissue has been fixed in formalin. In one embodiment for *Aspergillus terreus* or *Aspergillus niger* mycotoxin detection and quantitation, the tissue can then be processed by various dehydration steps and finally embedded in paraffin. In this embodiment, the tissue can then be cut in 3-5 micron samples. In an illustrative embodiment, approximately 25-35 mg of tissue can then be processed for mycotoxin extraction. Illustratively, body fluids can be prepared as described in Examples 1 and 3 or by other methods known in the art. In another illustrative embodiment, patient body fluids can be tested for the presence of *Aspergillus terreus* or *Aspergillus niger* mycotoxins. Illustratively, any antigen associated with an *Aspergillus terreus* or *Aspergillus niger* mycotoxin can be detected.

In one embodiment, the methods and compositions for detection and quantification of *Aspergillus terreus* or *Aspergillus niger* mycotoxins can be specific and sensitive. Methods and compositions utilizing antibody-based identification of mycotoxins are described, for example, in U.S. patent application Ser. No. 11/731,674 (published as U.S. Patent Publication No. US 2008/0014582), herein incorporated by reference in its entirety. In illustrative embodiments, Enzyme-Linked Immunosorbant Assay (ELISA), affinity chromatography, or a Luminex®-based assay can be used to detect mycotoxins produced by *Aspergillus terreus* or *Aspergillus niger*.

Another exemplary detection method for multiple mycotoxins in patient samples that have been exposed to *Aspergillus terreus* or *Aspergillus niger* is the Luminex® format. In one aspect of the invention, the Luminex® assay utilizes microspheres (beads) that are dyed with fluorochromes and that are coupled to antigens to detect antibodies, in patient body fluids or tissues, to *Aspergillus terreus* or *Aspergillus*

*niger* mycotoxins, or to *Aspergillus terreus* or *Aspergillus niger* mycotoxin antigens. In another embodiment, the microspheres are coupled to antibodies to detect, in patient body fluids or tissues, *Aspergillus terreus* or *Aspergillus niger* mycotoxins, or *Aspergillus terreus* or *Aspergillus niger* mycotoxin antigens. In this illustrative embodiment, the antibodies coupled to the microspheres can be polyclonal or monoclonal antibodies, but monoclonal antibodies are typically used. In another illustrative embodiment, the beads can be coupled to DNA probes to detect DNA specific to *Aspergillus terreus* or *Aspergillus niger*.

In the embodiment where mycotoxins are identified and quantitated, control samples of the body fluid or tissue to be analyzed can be obtained from patients with no documented history of exposure *Aspergillus terreus* or *Aspergillus niger*. For example, negative control samples can be obtained from autopsy specimens in which the patient had no exposure to *Aspergillus terreus* or *Aspergillus niger* (e.g., victims of motor vehicle accidents, coronary artery disease, or myocardial infarction). For positive controls, for example, samples of negative tissue and/or body fluids can be spiked with known positive amounts of *Aspergillus terreus* or *Aspergillus niger* mycotoxins or spores prior to evaluation to generate a calibration curve.

In another illustrative embodiment, a method is provided for identifying a patient at risk for an *Aspergillus terreus* fungal infection. The method comprises the steps of extracting and recovering DNA of the *Aspergillus terreus* fungal species from a tissue or a body fluid of the patient, amplifying the DNA, hybridizing a probe to the DNA to specifically identify the *Aspergillus terreus* fungal species, wherein the probe has a sequence of SEQ ID NO: 1, and specifically identifying the *Aspergillus terreus* fungal species.

In another illustrative embodiment, a method is provided for identifying a patient at risk for an *Aspergillus niger* fungal infection. The method comprises the steps of extracting and recovering DNA of the *Aspergillus niger* fungal species from a tissue or a body fluid of the patient, amplifying the DNA, hybridizing a probe to the DNA to specifically identify the *Aspergillus niger* fungal species, wherein the probe has a sequence of SEQ ID NO: 4, and specifically identifying the *Aspergillus niger* fungal species.

In some embodiments, the body fluid is selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma. In some embodiments, the probe is bound to a bead dyed with a fluorochrome.

In various embodiments, the method further comprises the step of developing an effective treatment regimen for the patient. In other embodiments, the method further comprises the step of administering an anti-fungal agent to the patient. Exemplary patients include cancer patients, post-operative patients, transplant patients, patients undergoing chemotherapy, immunosuppressed patients, and the like. In one embodiment, the patient is a transplant patient. Patients may experience symptoms of fungal infections including sinusitis, allergic reactions, headaches, and skin rashes. Patients include humans or animals.

In yet other embodiments, the method further comprises the step of testing for the presence of an *Aspergillus terreus* or *Aspergillus niger* mycotoxin in the tissue or the body fluid prior to extraction and recovery of the DNA. The methods related to the detection of mycotoxins described above are also applicable to the method of identifying a patient at risk for an *Aspergillus terreus* or *Aspergillus niger* fungal infection. In some embodiments, the testing for the presence of the *Aspergillus terreus* or *Aspergillus niger* mycotoxin comprises contacting the mycotoxin with an antibody directed against the mycotoxin.

In another illustrative embodiment, a method is provided for identifying a patient with an *Aspergillus terreus* fungal infection. The method comprises the steps of extracting and recovering DNA of the *Aspergillus terreus* fungal species from a tissue or a body fluid of the patient, amplifying the DNA, hybridizing a probe to the DNA to specifically identify the *Aspergillus terreus* fungal species, wherein the probe has a sequence of SEQ ID NO: 1, and specifically identifying the *Aspergillus terreus* fungal species. The various embodiments described above regarding identification of a patient at risk for an *Aspergillus terreus* fungal infection are also applicable to the embodiments regarding identifying a patient with an *Aspergillus terreus* fungal infection.

In another illustrative embodiment, a method is provided for identifying a patient with an *Aspergillus niger* fungal infection. The method comprises the steps of extracting and recovering DNA of the *Aspergillus niger* fungal species from a tissue or a body fluid of the patient, amplifying the DNA, hybridizing a probe to the DNA to specifically identify the *Aspergillus niger* fungal species, wherein the probe has a sequence of SEQ ID NO: 4, and specifically identifying the *Aspergillus niger* fungal species. The various embodiments described above regarding identification of a patient at risk for an *Aspergillus niger* fungal infection are also applicable to the embodiments regarding identifying a patient with an *Aspergillus niger* fungal infection.

In another illustrative embodiment, an isolated, purified nucleic acid is provided. In one embodiment, the isolated, purified nucleic acid comprises SEQ ID NO: 1 or a sequence that hybridizes under highly stringent conditions to a sequence comprising SEQ ID NO: 1. In another embodiment, the isolated, purified nucleic acid consists of SEQ ID NO: 1 or a sequence that hybridizes under highly stringent conditions to a sequence consisting of SEQ ID NO: 1. In yet another embodiment, the isolated, purified nucleic acid comprises SEQ ID NO: 2 or a sequence that hybridizes under highly stringent conditions to a sequence comprising SEQ ID NO: 2. In another embodiment, the isolated, purified nucleic acid consists of SEQ ID NO: 2 or a sequence that hybridizes under highly stringent conditions to a sequence consisting of SEQ ID NO: 2. In yet another embodiment, the isolated, purified nucleic acid comprises SEQ ID NO: 3 or a sequence that hybridizes under highly stringent conditions to a sequence comprising SEQ ID NO: 3. In another embodiment, the isolated, purified nucleic acid consists of SEQ ID NO: 3 or a sequence that hybridizes under highly stringent conditions to a sequence consisting of SEQ ID NO: 3. In various embodiments, the nucleic acid described in this paragraph can be isolated or purified.

In another illustrative embodiment, an isolated, purified nucleic acid is provided. In one embodiment, the isolated, purified nucleic acid comprises SEQ ID NO: 4 or a sequence that hybridizes under highly stringent conditions to a sequence comprising SEQ ID NO: 4. In another embodiment, the isolated, purified nucleic acid consists of SEQ ID NO: 4 or a sequence that hybridizes under highly stringent conditions to a sequence consisting of SEQ ID NO: 4. In yet another embodiment, the isolated, purified nucleic acid comprises SEQ ID NO: 5 or a sequence that hybridizes under highly stringent conditions to a sequence comprising SEQ ID NO: 5. In another embodiment, the isolated, purified nucleic acid consists of SEQ ID NO: 5 or a sequence that hybridizes under highly stringent conditions to a sequence consisting of SEQ ID NO: 5. In yet another embodiment, the isolated, purified nucleic acid comprises SEQ ID NO: 6 or a sequence that hybridizes under highly stringent conditions to a sequence comprising SEQ ID NO: 6. In another embodiment, the isolated, purified nucleic acid consists of SEQ ID NO: 6 or a sequence that hybridizes under highly stringent conditions to a sequence consisting of SEQ ID NO: 6. In various embodiments, the nucleic acid described in this paragraph can be isolated or purified.

In another illustrative embodiment, kits are provided. The kits are useful for identifying, detecting, or quantitating *Aspergillus terreus* or *Aspergillus niger* DNA or mycotoxins in a patient tissue or body fluid. In the embodiment where the kit is used to identify fungal DNA, the kit can contain the probes and/or primers described herein, components to extract and isolate fungal DNA, and/or components for DNA amplification, such as a heat stable DNA polymerase (e.g., Taq polymerase or Vent polymerase), buffers, $MgCl_2$, $H_2O$, and the like. In the embodiment where the kit is used to identify mycotoxins (i.e., a mycotoxin or a mycotoxin antigen), the kit can contain components to extract and isolate the mycotoxin (i.e., a mycotoxin or a mycotoxin antigen), antibody affinity matrices, ELISA plates, Luminex® beads, polyclonal or monoclonal antibodies, color development reagents, buffers, and the like. In one embodiment, the reagents can remain in liquid form. In another embodiment, the reagents can be lyophilized. In another illustrative embodiment, the kit can be used to detect other fungal antigens. The kits can also contain instructions for use.

In one embodiment, a kit comprising an isolated, purified nucleic acid with a sequence comprising SEQ ID NO: 1 is provided. In some embodiments, the kit comprises an isolated, purified nucleic acid with a sequence consisting of SEQ ID NO: 1.

In some embodiments, the kit further comprises an isolated, purified nucleic acid with a sequence comprising SEQ ID NO: 2 and an isolated, purified nucleic acid with a sequence comprising SEQ ID NO: 3. In other embodiments, the kit further comprises an isolated, purified nucleic acid with a sequence consisting of SEQ ID NO: 2 and a purified nucleic acid with a sequence consisting of SEQ ID NO: 3.

In one embodiment, a kit comprising an isolated, purified nucleic acid with a sequence comprising SEQ ID NO: 4 is provided. In some embodiments, the kit comprises an isolated, purified nucleic acid with a sequence consisting of SEQ ID NO: 4.

In some embodiments, the kit further comprises an isolated, purified nucleic acid with a sequence comprising SEQ ID NO: 5 and an isolated, purified nucleic acid with a sequence comprising SEQ ID NO: 6. In other embodiments, the kit further comprises an isolated, purified nucleic acid with a sequence consisting of SEQ ID NO: 5 and a purified nucleic acid with a sequence consisting of SEQ ID NO: 6.

In other embodiments, the kit further comprises components for the extraction and recovery of an *Aspergillus terreus* or *Aspergillus niger* mycotoxin from a body fluid or a tissue of a patient and components for identification of the mycotoxin. In some embodiments, the components for identification of the mycotoxin include beads dyed with a fluorochrome and coupled to antibodies to the mycotoxin or to a mycotoxin antigen. In some embodiments, the components for identification of the mycotoxin comprise an antibody directed against the mycotoxin.

A calibration reagent (or multiple calibration reagents) can also be included in the *Aspergillus terreus* or *Aspergillus niger* mycotoxin kit and "calibration reagent" means any standard or reference material containing a known amount of the mycotoxin (i.e., a mycotoxin or a mycotoxin antigen). The sample suspected of containing the *Aspergillus terreus* or *Aspergillus niger* mycotoxin and the calibration reagent (or multiple calibration reagents) are assayed under similar conditions. The *Aspergillus terreus* or *Aspergillus niger* mycotoxin concentration is then calculated by comparing the results obtained for the unknown sample with the results obtained for the calibration reagent(s).

In another aspect of the present disclosure, probes and primers for *Aspergillus niger* are provided. The probe and primers for *Aspergillus niger* are shown below. "Primer F" refers to a forward primer and "Primer R" refers to a reverse primer which are well-known terms in the art.

```
Target: Aspergillus niger
Probe:
                                         (SEQ ID NO: 4)
5'-TGTCTATTGTACCCTGTTGCTTC Primer F:
                                         (SEQ ID NO: 5)
5'-CGTAGGTGAACCTGCGGAAG Primer R:
                                         (SEQ ID NO: 6)
5'-ATCGATGCCGGAACCAAGAG
```

The following examples provide illustrative methods for carrying out the practice of the present invention. As such, these examples are provided for illustrative purposes only and are not intended to be limiting.

EXAMPLE 1

Samples and Sample Preparation

Tissue and body fluid samples can be prepared as follows. Human urine may be received in 5-10 ml quantities as first in the morning voided urines. Serums may be received with the blood clot removed prior to receipt. A minimum of 1 ml of serum can be frozen or used. Nasal secretions may be obtained from hospital patients or out-patients. Fixed autopsy and surgical biopsy specimens may be obtained from patients who had a history of exposure to mycotoxins or fungi. Samples can be obtained from hospital pathology departments or coroners' offices. Tissue samples and body fluid samples can also be obtained from patients who had no exposure to mycotoxins or fungi for sampling as a negative control group. Tissue specimens can be cut using procedures described in Example 2.

In an exemplary embodiment, specimens can be placed into two groups. Group 1 can comprise samples from individuals with no reported symptoms or known fungi or mycotoxin exposure. These samples can serve as negative controls and n values can differ in each group of specimens sampled. Group 2 can comprise samples from individuals with reported exposure to non-identified fungi or chemicals. Each test conducted can have a different n value. Common symptoms of patients corresponding to group 2 samples can include blurred vision, memory loss, fatigue, headache, nausea, loss of balance, cognitive deficits, rhinitis, sinusitis, rashes, and allergies. A detailed history and symptoms can be provided to correspond to each patient sample.

Nasal secretions and washings can be obtained by injection of 3-5 ml of sterile saline in each nostril of a patient. The patient can be instructed to hold the saline in the nostrils for 30 seconds and then blow the saline into a sterile container held close to the nose. The specimen(s) can then be collected and placed in containers.

Negative control samples of mycotoxins can be made by dilution techniques. Samples of extracted and filtered human heart tissue, liver tissue, urine, and nasal secretions (including sputum) can be spiked with various levels of the above named toxins. Each time a sample is evaluated, calibrators and negative and positive spiked tissues and fluids can also be evaluated. Statistical analyses on all types of samples for mycotoxins can be performed for sensitivity and specificity.

EXAMPLE 2

Preparation of Tissues for Mycotoxin Extraction

Preparation of tissues for myctotoxin extraction from formalin fixed tissue and paraffin-embedded tissue from humans or animals can be accomplished using the following procedure.
Specimens
Tissue may be received as either tissue fixed in a 10% formalin solution or in a paraffin-embedded tissue block. Tissue can be stored indefinitely in either form. However, because of cross-linking of formalin and proteins which may give false negative readings for DNA, the tissue may not be stored in formalin for greater than 6 months. A minimum of 25-35 mg of formalin-fixed tissue may be required for myctotoxin extraction. A maximum of 3 grams of formalin-fixed tissue can be used.
Materials
Phosphate Buffered Saline (PBS; 0.9%), acid-washed silica beads (Cat # G1277; obtained from Sigma-Aldrich), collection tubes (2 ml) screw cap, methanol (reagent grade, Sigma), and microcentrifuge tubes (2 ml) may be used.
Procedure
For silica beads, 0.3 g±0.01 g of silica bead beating glass can be added to a 2 ml screw cap tube making sure that there are no glass beads in the cap or around the rim. The tubes containing the beads can be sterilized in an autoclave on the dry cycle for 10 minutes. If a large amount of tissue is evaluated, the tissue can be placed in a blender and blended in PBS until well emulsified in the PBS. The sample can then be filtered using simple gravity filtration through Whatman #9 filter paper.
The samples may be recorded and assigned numbers in a sample log. 25-35 mg of paraffin-embedded tissue can be then weighed and placed in a 2.0 ml screw cap tube. Methanol can be added (1.0 ml reagent grade methanol) to the tube with the 0.3 g of silica beads and the sample vortexed for 1 minute. The samples can be bead beated on the bead beater for 1 minute at the speed of 45. Then 500 µl of sample can be removed and placed in 4.5 ml of PBS taking care not to remove the paraffin from the sample tube. The sample could then be used for extraction or could be frozen at −20 degrees centigrade to be used later in extraction and detection of mycotoxins.

EXAMPLE 3

Preparation of Body Fluids for Mycotoxin Detection

Urine may be received from a morning fresh first-voided specimen and stored at 1-6 degrees centigrade in a glass container. A urine analysis can be conducted using a dipstick to measure pH, specific gravity, glucose, nitrates, ketones, and blood. The urine can be examined for sediment and can be centrifuged at 2500 rpm for 5 minutes if sediment is present. The supernatant can be saved in a glass container for mycotoxin testing (storing in plastic may be avoided to avoid a decrease in the detection level of tricothecenes).

Nasal secretions and mucous samples as well as washes may be observed for mucous presence. If mucous is present, a solution of MUCOSOL™ (Alpha Tec Systems, Inc. Vancouver, Wash.) can be prepared and added in equal amounts of body fluid to MUCOSOL™ in the secretions containing mucous. The specimen may then be allowed to incubate 30 minutes at room temperature. The specimen was then centrifuged and the supernatant was removed. The sediment can then be re-suspended in 10 ml of PBS. The specimen can then be treated like any other body fluid and subjected to tests for identification. If testing for the presence of *Aspergillus terreus* DNA is desired, the specimen can then be subjected to the tests described in Example 4.

Blood samples may be obtained from the negative control group and exposed patients. Specimens may be allowed to clot (no anticoagulant added) and then centrifuged for 10 minutes at 2000 rpm. Specimens can be stored at 1-6 degrees centigrade for 48 hours or frozen at −20 degrees centigrade for an indefinite period of time. Blood samples can be extracted in a manner similar to that described by Garbis et al., Anal. Chem. 73:53589-64 (2001) and Hedman et al. Arch. Tieremahr. 50:13-24 (1997). Serum samples can be aliquoted in 200 µl amounts into sterile 1.5 ml polystyrene microcentrifuge tubes. Immediately, 600 µl of high performance HPLC grade acetonitrile (Fisher Scientific, Hampton, N.H.) can be added. After 15 minutes, the samples can be vortexed and centrifuged. The supernatants can be transferred into clean 1.5 ml glass vials. Each sample may be evaporated under a gentle stream of dry nitrogen and re-suspended in 100 µl of pre-warmed sterile water. In one embodiment, this can be the final working solution for ELISA assays. Spinal fluid samples can be analyzed as obtained from human patients. Samples may not be processed before analysis.

EXAMPLE 4

Detection of *Aspergillus Terreus* DNA

The primers and probes used for amplification and detection of *Aspergillus terreus* DNA are as follows:

```
Target: Aspergillus terreus
Probe:
                                       (SEQ ID NO: 1)
5'-AGTCTGAGTGTGATTCTTTGCAATC Primer F:
                                       (SEQ ID NO: 2)
5'-ACATGAACCCTGTTCTGAAAG Primer R:
                                       (SEQ ID NO: 3)
5'-CCAAGAGATCCATTGTTGAAAG
```

Extraction Methods:
  Bead Beater Tube Preparation:
  1. 0.3 g+0.01 g of silica bead beating glass (Sigma-Aldrich Cat. no G1277) was added to 2 ml screw cap tube avoiding glass beads in the cap or around the rim.
  2. The tubes containing the beads were sterilized in an autoclave on the dry cycle for 10 minutes.
  3. The tubes were removed from the autoclave (proceed to the next step).
  Solution Preparation:
  4. Buffers ATL (from DNAeasy® Tissue Kit, Cat. no. 69506 (Quiagen, Stanford Valencia, Calif.)) and AL (from DNAeasy® Tissue Kit, Cat. no. 69506) may form precipitates upon storage. If a precipitate formed in either buffer, the buffer was incubated at 55° C. until the precipitate fully dissolved.

5. Buffers AW1 and AW2 (from DNAeasy® Tissue Kit, Cat. no. 69506) were supplied as concentrates. Before using for the first time, the appropriate amounts of ethanol (96-100%) were added to Buffers AW1 and AW2 as indicated on the bottles.
6. A 55° C. heat block and a 70° C. heat block were prepared for use in the assay.

Preparation of the Spore Solution or Tissue:

7. If frozen material was used, it was equilibrated to room temperature.
8. About 25.0 mg of paraffin-embedded tissue was weighed or 10.0 μl of spore solution was placed in a 2.0 ml screw cap tube.
9. 180.0 μl of ATL Buffer and 20.0 μl of Proteinase K was added to each sample making sure that the lysate was not gelatinous.
10. 10.0 μl of the Geo Spore reference DNA was added to each sample. (See Assay Specific Procedure for information regarding internal and external controls)
11. All samples were bead beated on the Bead Beater for 1 minute at the speed of 45.
12. Samples were incubated at 55° C. on a pre-warmed heat block for 1 hour.

Extraction of Nucleic Acid:

15. The samples were removed from the heat block and vortexed 15 seconds.
16. 200 μl of Buffer AL was added and incubated at 70° C. for 10 minutes.
17. The tubes were removed from the 70° C. heat block and add 200 μl of ethanol
18. 200 μl of ethanol was added to each tube and vortexed.
19. The mixture underneath the layer of paraffin was pipetted for each sample, making sure not to pipette the silica beads, into the corresponding DNeasy® Mini Spin Column 2 ml collection tube combo for that sample.
20. The columns were centrifuged in a microcentrifuge at 8000 RPM for 1 minute. The collection tube containing the flow through was discarded.
21. Each spin column was placed in a new 2.0 ml collection tube.
22. 500.0 μl of Buffer AW1 was added to each column and centrifuged at 8000 RPM for 1 minute. The collection tube containing the flow through was discarded.
23. Each spin column was placed in a new 2.0 ml collection tube.
24. 500.0 μl of Buffer AW2 was added to each column and centrifuged at 13,000 RPM for 5 minute.
25. The spin columns were removed carefully from the collection tubes so as not to splash nozzles. The collection tube containing the flow through was discarded.
26. The spin columns were placed in their corresponding 1.5 ml elution tube.
27. 100.0 μl of Buffer AE (from DNAeasy® Tissue Kit, Cat. no. 69506) was placed into each spin column and incubated for 3 minutes at room temperature.
28. The spin columns were centrifuged at 8000 RPM for 1 minute. The spin columns were discarded and capped and the extracted nucleic acid samples were stored at −20° C.

Real-Time PCR:

Preparation and Reaction Setup

1. Dilution of Probe Stocks
    a. Resuspend the lyophilized probes in PCR grade water to a final concentration of 100 μM.
        (Example: If the synthesis yields 15.03 nMoles, add 150.3 of PCR grade water to achieve 100 μM concentration)
2. Dilution of Primer Stocks
    a. Resuspend the lyophilized primers in PCR grade water to a final concentration of 100
        (Example: If the synthesis yields 38.6 nMoles, add 386 μl of PCR grade water to achieve 100 μM concentration)
3. Preparation of Primer/Probe Working Stock
    a. Example Working Stock setup for *Aspergillus terreus* (Use 3.5 μl of this working stock for each reaction performed):

| P1 100 uM | P2 100 uM | Probe 100 uM | MgCl2 1 M | Final Conc. | Water | Final Volume |
|---|---|---|---|---|---|---|
| 15.0 uL | 15.0 uL | 10.0 uL | NA | NA | 660 uL | 700 uL |

The assay for *Aspergillus terreus* was optimized utilizing target DNA in 10 fold serial dilutions formulating a curve. Data was collected and evaluated and the assay was optimized.

4. Reaction Setup
    a. The reaction setup for one *Aspergillus terreus* reaction is shown below.

| DNA | 5.0 μl |
|---|---|
| Primer/Probe Working Stock | 3.5 μl (Final Concentration see appendix A) |
| OmniMix Beads | 0.5 μl Beads (no volume contribution) |
| PCR Grade Water | 16.5 μl |
| Total | 25.0 μl |

See Example PCR Worksheet: (Note: sheet has been truncated to show 3 target sets):

II. Master Mix Setup

| Set 2 | Reagent | Lot # | Volume (uL) | Reaction No. | Total Amount | Target |
|---|---|---|---|---|---|---|
| 1 | H2O | 66k2339 | 16.5 | 8 | 132.0 | *A. Terreus* |
| 2 | P/P Working Stock | CURRENT | 3.5 | 8 | 28.0 | |
| 3 | Omni Mix (Bead) | 1706 | 0.5 | 8 | 4.0 | |
| 4 | MgCl2 | NA | 0.0 | 0 | 0.0 | |

*Add MgCl$_2$ as needed per target subtract volume used from water added to maintain a 20 μl reaction. Add 20 μl of Master Mix to each tube and then add 5.0 μl of template for a total volume of 25.0 μl.

5. Smart Cycler Cycling Parameters (Omni Fungal I)
   a. Omni Fungal I is the primary program used for the fungal real time assays and the run parameters for this program are outlined below. Cases may occur where changes to this program may be necessary for a specific target or specimen type.
   Step 1 (1 Cycle)
   Hot Start: 95° C. for 120 seconds
   Step 2 (45 cycles)
   Denature: 95° C. for 5 seconds
   Anneal: 60° C. for 45 seconds Master Mix Preparation:
1. All steps were performed under sterile conditions.
2. After the water and beads had been pipetted into to the individual tubes, the tubes were mixed until the beads (Cat no. Omni 1-100N-050; Cepheid, Sunnyvale, Calif.) were completely dissolved.
3. After the beads were dissolved, the primer/probe working stock was pipetted into each master mix tube as described in the PCR worksheet.
4. The solutions were mixed completely and the working stocks returned to the −20° C. freezer.
5. Controls—
   a. Internal Control—Every clinical sample processed was inoculated with spores from the internal control target Geometrica to show that a negative target result is a true negative result and not related to the extraction of the sample. The samples were processed through the extraction protocol and amplified and detected utilizing primer and probes specific for Geometrica.
   b. Positive Control—A positive control for *Aspergillus terreus* (Primer/Probe sets) was processed along with each clinical sample in each real-time PCR run. This positive control can be extracted from tissue or spore solutions but must be lot checked prior to use. The positive control shows that the primer/probe set for each target is not being inhibited and shows that a negative result is a true negative.
   c. Negative Control—A negative control for *Aspergillus terreus* (Primer/Probe sets) was processed along with each clinical sample in each real-time PCR run. This negative control can be extracted from tissue or water but must be lot checked prior to use. The negative control shows that the primer/probe set, water and extraction reagents for each target is not contaminated with the target and shows that a positive result is a true positive.

Addition of Target Nucleic Acid:
1. 5.0 μl of the negative control, positive control and patient samples was pipetted into the appropriate reaction tubes.
2. The reaction tubes were centrifuged using the Smart Cycler® II modified centrifuge.
3. The tubes were returned to the cooling block and stored at 4° C. or the Smart Cycler Setup and Run was conducted.

Smart Cycler Setup and Run:
1. The Omni Fungal I protocol or the appropriate protocol was selected for this real-time run.
2. For information regarding the operation of the Smart Cycler see SmartCycler Operation (20.2008S) (Smart Cycler® II Instrument; Cepheid, Sunnyvale, Calif.).
3. Probes may have a FAM fluorophore on the 5' end of the sequence and a BHQI quencher on the 3' end of the sequence.
4. Primers and probes may be ordered from Biosearch or Operon/MWG.

Data Analysis:
1. After the run is completed the results were analyzed by reviewing each site in the results table. If a specific sample tested was registered as positive by the software there was a positive in the results column for that sample. There was also a crossing point registered in the Ct column for that sample.
2. After reviewing the Results Table, the curves were reviewed for each sample by selecting the "FAM" or "Log FAM" of the "Views" menu.
3. With the graph selected, all samples that created a curve were present on the screen. Each sample was reviewed independently by clicking on the Site ID associated with the sample of interest located just to the right of the graph.
4. A sample was analyzed as positive by the software if the curve broke the baseline of 30 (default set in section above) before the end of the 45 cycles and negative if it did not break the baseline of 30 before the end of the 45 cycles.
5. Each sample was reviewed and then highlighted so that all sample curves were present on the graph.

Results Interpretation:
1. Positive Result: A positive result is defined as any amplification observed crossing a baseline fluorescence of >30 between cycles 1 and 40 of the real-time PCR run.
2. Negative Result: A negative result is defined as no amplification observed crossing a baseline fluorescence of >30 between cycles 1 and 40 of the PCR run.
3. Equivocal Result: An equivocal result is defined as no amplification observed crossing a baseline fluorescence of >30 between cycles 1 and 40, a control out of range or questions regarding sample integrity.
4. Positive Control: A control that is positive for the target being tested and shows that the assay will show a positive in the presence of target spores and that there is not PCR inhibition.
5. Negative Control: A control that is negative for the target being tested and shows that the reagents or the sample were not contaminated with the target prior to the testing of the sample.
6. Internal Control: A control used to show that the extraction process is working fine for the purification of nucleic acid from the clinical specimen and that a negative result is truly negative and not due to an issue associated with the extraction. (Note: the internal control must be positive for any sample to be reported as negative for a target.)

See Table Below:

|  | Crossing Point | Positive Control | Negative Control | Internal Control |
|---|---|---|---|---|
| Reportable Result |  |  |  |  |
| Positive Result | ≥40 | (+) | (−) | (+) |
| Positive Result | ≥40 | (−) | (−) | (+) |
| Positive Result | ≥40 | (+) | (−) | (−) |
| Positive Result | ≥40 | (−) | (−) | (−) |
| Negative Result | (−) | (+) | (−) | (+) |
| Negative Result | (−) | (+) | (+) | (+) |

-continued

|  | Crossing Point | Positive Control | Negative Control | Internal Control |
|---|---|---|---|---|
| Negative Result Unreportable Result | (−) | (−) | (+) | (+) |
| Positive Result | ≥40 | (+) | (+) | (+) |
| Positive Result | ≥40 | (−) | (+) | (+) |
| Positive Result | ≥40 | (+) | (+) | (−) |
| Positive Result | ≥40 | (−) | (+) | (−) |
| Negative Result | (−) | (−) | (−) | (+) |
| Negative Result | (−) | (+) | (−) | (−) |
| Negative Result Equivocal Result | (−) | (+) | (+) | (−) |
| Case by Case | Case by Case | Case by Case | Case by Case | Case by Case |

In other illustrative embodiments, results can be determined based on a cycle range between cycles 1 and 45 of the PCR run or other useful ranges can be used.

DNA RESULTS

Results are shown in the following table for the standard curve samples of *Aspergillus terreus*, as well as the negative and positive controls. For the *Aspergillus terreus* sample, the probe and primers described herein (i.e., SEQ ID NO: 1, SEQ ID NO: 2, and SEQ ID NO: 3) were utilized.

| Sample Name | Presence of DNA | Crossing Point (Ct) |
|---|---|---|
| *A. terreus* Point 1 | Positive | 17.50 |
| *A. terreus* Point 1 | Positive | 17.34 |
| *A. terreus* Point 2 | Positive | 21.11 |
| *A. terreus* Point 2 | Positive | 21.14 |
| *A. terreus* Point 3 | Positive | 25.16 |
| *A. terreus* Point 3 | Positive | 25.03 |
| Negative Control | Negative | ≥40 |
| Negative Control | Negative | ≥40 |

The *A. terreus* Point 1 values in the above table represent the positive control for the standard curve. The *A. terreus* Point 2 values in the above table represent a 1:10 dilution. The *A. terreus* Point 3 values in the above table represent a 1:100 dilution.

EXAMPLE 5

Detection of Mycotoxins Using Luminex®

The purpose of this assay is to utilize the Luminex® platform to detect mycotoxins in patient samples that have been exposed to fungal targets. The Luminex® assay utilizes microspheres (beads) that are coupled to antigens to detect antibodies against those specific antigens in a sample. Samples and coupled microspheres will be incubated in microtitration filter wells where antigen-antibody binding occurs. After incubation and washing, the appropriate detection antibody (e.g., biotinylated antibody) will be introduced and incubated during which antibody-antibody binding occurs. After incubation and washing, a reporter conjugate will be added and incubated where the biotin-binding reaction occurs.

In theory, each microsphere is color-coded into 100 different sets. Each bead set can be coated with a reagent to capture and detect a specific analyte from a sample. The Luminex® 100 has lasers that excite the internal dyes that identify the microsphere and any reporter dye captured during the assay. During the run on the Luminex®, several readings will be made on each of the bead sets. Potentially, this will create a multiplexing capability of up to 100 unique assays with one single sample.

EXAMPLE 6

Luminex Assay Using DNA Probes Bound to Beads

Microspheres (Luminex Corporation, Austin, Tex.) are 5.6 µm in diameter and are comprised of polystyrene, divinyl benzene, and methacrylic acid with surface carboxylate functionality for covalent attachment of biomolecules. The microspheres are internally dyed with red, infrared-emitting fluorochromes. Spectral addresses can be created by adjusting the concentrations of each fluorochrome with each bead set. When the microsphere sets are analyzed with the Luminex 100 instrument (Luminex), each bead set can be identified and classified by a distinct fluorescence signature pattern.

EXAMPLE 7

Luminex Indirect Assay Using Antigen Bound to Beads

Microspheres (Luminex Corporation, Austin, Tex.) are 5.6 µm in diameter and are comprised of polystyrene, divinyl benzene, and methacrylic acid with surface carboxylate functionality for covalent attachment of biomolecules. The microspheres are internally dyed with red, infrared-emitting fluorochromes. Spectral addresses can be created by adjusting the concentrations each fluorochrome with each bead set. When the microsphere sets are analyzed with the Luminex 100 instrument (Luminex®), each bead set can be identified and classified by a distinct fluorescence signature pattern.

EXAMPLE 8

Development and Specificity Testing of *Aspergillus Terreus* DNA Probes and Primers The following sequences represent the designs that were developed and tested for *Aspergillus terreus*. Assays were designed, modeled, and tested in the laboratory. Assays that generated results were then tested for specificity, efficiency, and precision.

```
Design 1:
Probe:
                              (SEQ ID NO: 1)
5'-AGTCTGAGTGTGATTCTTTGCAATC

F:
                              (SEQ ID NO: 2)
5'-ACATGAACCCTGTTCTGAAAG

R:
                              (SEQ ID NO: 3)
5'-CCAAGAGATCCATTGTTGAAAG
```

-continued

Design 2:
AP1:
(SEQ ID NO: 7)
5'-GAATCATCGAGTCTTTGAACGCACA

AF1:
(SEQ ID NO: 8)
5'-GGCATCGATGAAGAACGCAG

AR1:
(SEQ ID NO: 9)
5'-TGACGCTCGGACAGGCATG

Design 3:
AP2:
(SEQ ID NO: 10)
5'-GAAGAACGCAGCGAAATGCGATAA

AF2:
(SEQ ID NO: 11)
5'-GATCTCTTGGTTCCGGCATC

AR2:
(SEQ ID NO: 12)
5'-GCAATGTGCGTTCAAAGACTC

For each probe and primer design, DNA samples of *Aspergillus niger, Aspergillus flavus, Aspergillus fumigatus*, and *Aspergillus terreus* were compared to determine specificity in identifying *Aspergillus terreus* DNA. The results of the three designs are shown in the following table:

| Specificity: *Aspergillus terreus* - Design 1 Selected- Designs 2 and 3 not specific | | | | |
|---|---|---|---|---|
| | A. niger | A. flavus | A. fumigatus | A. terreus |
| Design 1 | Not Detected | Not Detected | Not Detected | Detected |
| Design 2 | Detected | Detected | Detected | Detected |
| Design 3 | Detected | Detected | Detected | Detected |

Design 1 detected DNA from *Aspergillus terreus*. However, Design 1 did not detect DNA of *Aspergillus niger, Aspergillus flavus*, or *Aspergillus fumigatus*. Therefore, Design 1 demonstrated specificity for the identification of *Aspergillus terreus* DNA, demonstrating 100% efficiency.

In comparison, Design 2 and Design 3 detected DNA from each of *Aspergillus niger, Aspergillus flavus, Aspergillus fumigatus*, and *Aspergillus terreus*. Therefore, Design 2 and Design 3 were not specific for the identification of *Aspergillus terreus* DNA.

EXAMPLE 9

Development and Specificity Testing of *Aspergillus Niger* DNA Probes and Primers The following sequences represent the designs that were developed and tested for *Aspergillus niger*. Assays were designed, modeled, and tested in the laboratory. Assays that generated results were then tested for specificity, efficiency, and precision.

Design 1:
Probe:
(SEQ ID NO: 4)
5'-TGTCTATTGTACCCTGTTGCTTC

F:
(SEQ ID NO: 5)
5'-CGTAGGTGAACCTGCGGAAG

R:
(SEQ ID NO: 6)
5'-ATCGATGCCGGAACCAAGAG

Design 2:
AP1:
(SEQ ID NO: 13)
5'-GAATCATCGAGTCTTTGAACGCACA

AF1:
(SEQ ID NO: 14)
5'-GGCATCGATGAAGAACGCAG

AR1:
(SEQ ID NO: 15)
5'-TGACGCTCGGACAGGCATG

Design 3:
AP2:
(SEQ ID NO: 16)
5'-GAAGAACGCAGCGAAATGCGATAA

AF2:
(SEQ ID NO: 17)
5'-GATCTCTTGGTTCCGGCATC

AR2:
(SEQ ID NO: 18)
5'-GCAATGTGCGTTCAAAGACTC

For each probe and primer design, DNA samples of *Aspergillus niger, Aspergillus flavus, Aspergillus fumigatus*, and *Aspergillus niger* were compared to determine specificity in identifying *Aspergillus niger* DNA. The results of the three designs are shown in the following table:

| Specificity: *Aspergillus niger* - Design 1 Selected- Designs 2 and 3 not specific | | | | |
|---|---|---|---|---|
| | A. niger | A. flavus | A. fumigatus | A. terreus |
| Design 1 | Detected | Not Detected | Not Detected | Not Detected |
| Design 2 | Detected | Detected | Detected | Detected |
| Design 3 | Detected | Detected | Detected | Detected |

Design 1 detected DNA from *Aspergillus niger*. However, Design 1 did not detect DNA of *Aspergillus fumigatus, Aspergillus flavus*, or *Aspergillus terreus*. Therefore, Design 1 demonstrated specificity for the identification of *Aspergillus niger* DNA, demonstrating 94.5% efficiency.

In comparison, Design 2 and Design 3 detected DNA from each of *Aspergillus niger, Aspergillus flavus, Aspergillus fumigatus*, and *Aspergillus terreus*. Therefore, Design 2 and Design 3 were not specific for the identification of *Aspergillus niger* DNA.

The invention claimed is:

1. A method of identifying an *Aspergillus niger* fungal species in a patient tissue or a patient body fluid, the method comprising the steps of:
   extracting and recovering DNA of the *Aspergillus niger* fungal species from the patient tissue or the patient body fluid;
   amplifying the DNA;
   hybridizing a probe to the DNA to specifically identify the fungal species, wherein the probe consists of SEQ ID NO: 4; and
   specifically identifying the *Aspergillus niger* fungal species.

2. The method of claim 1 further comprising using a forward primer and a reverse primer to amplify the DNA, wherein the forward primer consists of SEQ ID NO: 5 and the reverse primer consists of SEQ ID NO: 6.

3. The method of claim 1, wherein the DNA is amplified using PCR.

4. The method of claim 3, wherein the PCR is real-time PCR.

5. The method of claim 1, wherein the probe is fluorescently labeled.

6. The method of claim 1, wherein the probe is bound to a bead dyed with a fluorochrome.

7. The method of claim 1, wherein the amplified DNA is internal transcribed spacer regions of nuclear ribosomal DNA.

8. The method of claim 1, wherein the body fluid is selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma.

9. The method of claim 1, wherein the method further comprises the step of administering an anti-fungal agent to the patient.

10. The method of claim 1, wherein the patient is a transplant patient.

* * * * *

SEQUENCE LISTING

<160> NUMBER OF SEQ ID NOS: 18

<210> SEQ ID NO 1
<211> LENGTH: 25
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 1
agtctgagtg tgattctttg caatc                                          25

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acatgaaccc tgttctgaaa g                                              21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccaagagatc cattgttgaa ag                                             22

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
tgtctattgt accctgttgc ttc                                            23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgtaggtgaa cctgcggaag                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atcgatgccg gaaccaagag                                                20

<210> SEQ ID NO 7
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 7
gaatcatcga gtctttgaac gcaca                                           25

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggcatcgatg aagaacgcag                                                 20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgacgctcgg acaggcatg                                                  19

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
gaagaacgca gcgaaatgcg ataa                                            24

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatctcttgg ttccggcatc                                                 20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcaatgtgcg ttcaaagact c                                               21

<210> SEQ ID NO 13
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 13
gaatcatcga gtctttgaac gcaca                                          25

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggcatcgatg aagaacgcag                                                20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgacgctcgg acaggcatg                                                 19

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
gaagaacgca gcgaaatgcg ataa                                           24

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gatctcttgg ttccggcatc                                                20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcaatgtgcg ttcaaagact c                                              21
```